United States Patent [19]
Aristoff

[11] Patent Number: 5,238,954
[45] Date of Patent: Aug. 24, 1993

[54] FLUORINATED FLAVONE ACETIC ACID

[75] Inventor: Paul A. Aristoff, Portage, Mich.

[73] Assignee: The Upjohn Company, Kalamazoo, Mich.

[21] Appl. No.: 721,613

[22] PCT Filed: Dec. 11, 1989

[86] PCT No.: PCT/US89/05446
§ 371 Date: Jul. 18, 1991
§ 102(e) Date: Jul. 18, 1991

[51] Int. Cl.$^5$ .............. A61K 31/35; C07D 311/30
[52] U.S. Cl. ........................ 514/456; 549/403; 546/196; 544/151; 514/320; 514/233.5
[58] Field of Search ........... 549/403; 514/456, 320, 514/233.5; 546/196; 544/151

[56] References Cited

U.S. PATENT DOCUMENTS

| | | | |
|---|---|---|---|
| 4,602,034 | 7/1986 | Briet et al. | 514/456 |
| 4,783,533 | 11/1988 | Briet et al. | 514/456 |
| 5,116,954 | 5/1992 | Briet et al. | 534/551 |

FOREIGN PATENT DOCUMENTS

278176A2  8/1988  European Pat. Off. .

OTHER PUBLICATIONS

Atassi, G., et al., "Synthesis and Antitumor Activity of Some 8-Substituted-4-oxo-4H-1-benzopyrans," Eur. J. Med. Chem. 20(5):393-402 (1985).
Zee-Cheng, R. K-Y. and C. C. Cheng, "Flavoneacetic Acid," Drugs of the Future 12(2):123-125 (1987).
Weiss, R. B., et al., "Phase I and Clinical Pharmacology Study of Intravenous Flavone Acetic Acid (NSC 347512)[1]," Cancer Research 48:5878-5882 (1988).

Primary Examiner—Nicky Chan
Attorney, Agent, or Firm—Donald L. Corneglio

[57] ABSTRACT

A fluorinated flavone acetic acid suitable for use as an antitumor agent. Pharmaceutical compositions comprising the fluorinated flavone acetic acid and a pharmaceutically acceptable carrier. An antitumor composition comprising an antitumor effective amount of a fluorinated flavone acetic acid in a pharmaceutically acceptable carrier.

10 Claims, No Drawings

FLUORINATED FLAVONE ACETIC ACID

BACKGROUND OF THE INVENTION

The present invention is directed toward novel fluorinated flavone acetic acids (FAA) suitable for use as antitumor agents. The fluorinated FAA compounds are more effective than their unfluorinated counterparts. For example B. Derwinko and L-Y. Yang, "The Activity of flavone acetic acid (NSC 347512) on human colon cancer cells in vitro" Invest. New Drugs, 4:289–93 (1986) disclose that FAA (4-oxo-2-phenyl-4H-1-benzopyran-8-acetic acid) had "relatively poor cytotoxic effects and because the therapeutic range of FAA is so narrow, we conclude that this agent will not be a valuable contribution to the antitumor arsenal at least for colon cancer." Meanwhile, the fluorinated FAA of the present invention has shown curative activity in murine pancreatic carcinoma models and against solid tumors. In particular, they have been shown to exhibit activity against human tumor cell lines and an FAA resistant cell line.

INFORMATION DISCLOSURE

U.S. Pat. Nos. 4,783,533 and 4,602,034 disclose FAA compounds chemically called (4-oxo-4H-(1)-benzopyran-8-yl)alconic acids their salts and derivatives as well as methods for their preparation and use in the control of tumors. European Patent Application 0278176 discloses various flavone acetic acid analogs described as xanthenone-4-acetic acid. The synthesis and antitumor effect of substituted 4-oxo-4H-1-benzopyrans are described in Eur. J. Med. Chem., 20, 5, p. 393–402 (1985) which was authored by the same inventors of 4,783,533 and 4,602,034.

FAA compounds, particularly a diethylaminoethyl ester derivative are discussed in Drugs of the Future, Vol. 12, 2, p. 123–25 (1987). An article in Cancer Research, 48, 5878–82 (Oct. 15, 1988) entitled "Phase I and Clinical Pharmacology Study of Intravenous Flavone Acetic Acid" by Weiss, et al. describes the basic antitumor effects of FAA and results when administered to patients. FAA is reported to have murine tumor activity in animals although no objective tumor response was observed in humans tested. The article also reports the toxicity problems associated with FAA such as acute hypotension and generalized fatigue and asthemia.

SUMMARY OF THE INVENTION

In one aspect the subject invention is a compound according to Formula I wherein $R_1$ is CHO, CN, $CO_2M$, $CO_2R_3$ or $CONR_3R_4$ where M is hydrogen or a pharmaceutically acceptable salt such as Li, Na, K, Ca or other acceptable counter-ion for carboxylic acids, $R_3$ and $R_4$ are independently hydrogen, $C_1-C_{12}$ alkyl or heterosubstituted alkyl, $C_3-C_{10}$ cycloalkyl or heterosubstituted cycloalkyl, $C_6-C_{12}$ aryl, alkylaryl or are joined to form a $C_3-C_{10}$ cycloalkyl or heterosubstituted cycloalkyl; $R_2$ is hydrogen, fluorine, methyl, $CF_3$, phenyl or substituted phenyl. The fluorinated phenyl ring can be fluorinated at any of the C2 to C6 positions and n is 1 to 5, inclusive. Preferably, $R_1$ is $CO_2M$ and $R_2$ is hydrogen.

Typical fluorinated phenyl rings can include 3-fluorophenyl, 2,3,4,5-tetrafluorophenyl, pentafluorophenyl, 3,4-difluorophenyl, 2-fluorophenyl, 4-fluorophenyl, 2,6-difluorophenyl, 3,5-difluorophenyl, 3,4,5-trifluorophenyl, 2,3,5,6-tetrafluorophenyl, 2,3-difluorophenyl, 2,3,4-trifluorophenyl, 2,4,6-trifluorophenyl, 2,5-difluorophenyl or 2,4-difluorophenyl. Preferred compounds include 4-oxo-2-(3-fluorophenyl)-4H-1-benzopyran-8-acetic acid, 4-oxo-2-(pentafluorophenyl)-4H-1-benzopyran-8-acetic acid, 4-oxo-2-(3,4-difluorophenyl)-4H-1-benzopyran-8-acetic acid, 4-oxo-2-(2-fluorophenyl)-4H-1-benzopyran-8-acetic acid, 4-oxo-2-(4-fluorophenyl)-4H-1-benzopyran-8-acetic acid, 4-oxo-2-(2,6-difluorophenyl)-4H-1-benzopyran-8-acetic acid, or 4-oxo-2-(3,5-difluorophenyl)-4H-1-benzopyran-8-acetic acid, 4-oxo-2-(3,4-difluorophenyl)-4H-1-benzopyran-8-acetic acid, 4-oxo-2-(pentafluorophenyl)-4H-1-benzopyran-8-acetic acid, 4-oxo-2-(3,4,5-trifluorophenyl)-4H-1-benzopyran-8-acetic acid, 4-oxo-2-(2,3,5,6-tetrafluorophenyl)-4H-1-benzopyran-8-acetic acid, 4-oxo-2-(2,3-difluorophenyl)-4H-1-benzopyran-8-acetic acid, 4-oxo-2-(2,3,4-trifluorophenyl)-4H-1-benzopyran-8-acetic acid, 4-oxo-2-(2,4,6-trifluorophenyl)-4H-1-benzopyran-8-acetic acid, 4-oxo-2-(2,5-difluorophenyl)-4H-1-benzopyran-8-acetic acid or 4-oxo-2-(2,4-difluorophenyl)-4H-1-benzopyran-8-acetic acid.

In another aspect the subject invention is directed toward a pharmaceutical composition comprising an effective amount of a compound according to Formula I described above and a pharmaceutically acceptable carrier.

In yet another aspect the subject invention is directed toward an antitumor composition comprising an antitumor effective amount of a compound according to Formula I and a pharmaceutically acceptable carrier.

Generally, the fluorinated flavone acetic acid compounds have been discovered to have antitumor activity superior to unflourinated flavone acetic acid compounds. In addition, the fluorinated flavone acetic acids appear to have less toxic effects in animals than the unfluorinated flavone acetic acids.

DETAILED DESCRIPTION OF THE INVENTION

The present invention is directed to fluorinated FAA compounds represented by the structural formula I. Wherein $R_1$ is CHO, CN, $CO_2M$, $CO_2R_3$ or $CONR_3R_4$ where M is hydrogen or a pharmaceutically acceptable salt such as Li, Na, K, Ca or other acceptable counter-ion for carboxylic acids, $R_3$ and $R_4$ are independently hydrogen, $C_1-C_{12}$ alkyl or heterosubstituted alkyl, $C_3-C_{10}$ cycloalkyl or heterosubstituted cycloalkyl, $C_6-C_{12}$ aryl, alkylaryl or where they are joined to form a $C_3-C_{10}$ cycloalkyl or heterosubstituted cycloalkyl (and are attached to the proximate nitrogen). $R_2$ is hydrogen, fluorine, methyl, $CF_3$, phenyl or substituted phenyl. $NR_3R_4$ can be morpholino, piperidino, diethylaminoethyl or dimethylaminoethyl.

The fluorinated phenyl ring can be fluorinated at any of the C2 to C6 positions and n is 1 to 5 inclusive. Typical fluorinated phenyl ring structures can include 3-fluorophenyl, 2,3,4,5-tetrafluorophenyl, pentafluorophenyl, 3,4-difluorophenyl, 2-fluorophenyl, 4-fluorophenyl, 2,6-difluorophenyl, 3,5-difluorophenyl, 3,4,5-trifluorophenyl, 2,3,5,6-tetrafluorophenyl, 2,3-difluorophenyl, 2,3,4-trifluorophenyl, 2,4,6-trifluorophenyl, 2,5-difluorophenyl or 2,4-difluorophenyl.

Examples of "$C_1-C_{12}$ alkyl" are one to twelve carbon atom chains from methyl to dodecyl and isomeric forms thereof. Examples of "$C_3-C_{10}$ cycloalkyl" are three to ten carbon atoms formed in a ring such as cyclopropyl, cyclobutyl, cyclopentyl and cyclohexyl. Examples of "aryl" are six to twelve carbon atom rings which can be substituted with one to three hydroxy, $C_1$-$C_3$ alkyl, trifluoromethyl, fluoro, chloro or bromo group such as phenyl, α-naphthyl, β-naphthyl, m-methylphenyl, p-trifluoromethylphenyl and the like. "Alkylaryl" are seven to twenty-four carbon atoms from a $C_1$-$C_{12}$ alkyl and a $C_6$-$C_{12}$ aryl as defined.

The "heterosubstituted" forms of the alkyl and cycloalkyl groups are when a carbon in the chain or ring structure is replaced by a heteroatom such as nitrogen, oxygen or sulfur, for example, piperidino and morpholino. The heteroatom can then contain further alkyl, aryl or cycloalkyl groups to complete the valence, for example, dimethylaminoethyl or diethylaminoethyl. "Substituted phenyl" is a phenyl ring having a substituent pending therefrom such as fluorine, chlorine or bromine, hydroxy, or a $C_1$-$C_4$ alkyl group.

These compounds can be prepared by one or more methods described below as well as in accordance with the synthesis schemes disclosed in U.S. Pat. Nos. 4,783,533 and 4,602,034, herein incorporated by reference, utilizing the appropriate fluorinated phenyl ring as depicted in Formula I.

Generally the fluorinated FAA's of the present invention can be prepared as depicted in Schemes 1 or 2, below. In both Schemes 1 and 2, the various steps are well known in the art. That is, in Scheme 1, step 1 involves a Claisen-condensation of the β-ketoesters. Step 2 is a Simonis-type reaction, acid catalyzed β-ketoester condensation, such as with polyphosphoric acid, or phosphoric acid and phosphorous pentoxide. Step 3 is a radical catalyzed benzylic bromination, such as with N-bromosuccinimide in carbon tetrachloride. Step 4 involves the conversion of bromide to nitrile, a displacement using potassium cyanide and potassium iodide. Finally, Step 5 is the hydrolysis of nitrile to acid using, for example, acetic acid, water and sulfuric acid.

In Scheme 2, step 1 is a phenol alkylation which can employ allyl bromide and a base such as potassium carbonate or potassium hydroxide. Step 2 is Claisen rearrangement either by heating or by a Lewis acid treatment. Step 3 is an Allan-Robinson type reaction to prepare flavones such as disclosed in P. K. Jain, et al., Synthesis, pp. 221-22 (1982). Step 4 is an oxidation of the allyl group directly to an acid, for example by using $RuCl_3$, $NaIO_4$ or $NaIO_4$, $KMnO_4$ or ozonolysis followed by ozonide oxidation with hydrogen peroxide. Step 5 is the oxidation of the allyl group to an aldehyde. This can be accomplished by ozonolysis or osmium tetroxide/sodium periodate or with $RuCl_3$/$NaIO_4$. Finally, Step 6 is the oxidation of the aldehyde to an acid such as by sodium chlorite oxidation or silver oxide oxidation.

The fluorinated FAA compounds are more effective as antitumor agents than their unfluorinated analogs as is demonstrated by the in vitro and in vivo experiments.

The subject compounds can be effectively administered intraperitoneally, orally, subcutaneously or intravenously. A pharmaceutical composition of this invention contains as its active ingredient the fluorinated FAA compound associated or admixed with an acceptable vehicle or pharmaceutical excipient in suitable form for administration.

Unit doses may be sugar-coated pills, tablets, capsules, gellules, phials or bottles. The dosage forms contain between 50 and 1000 mg of active ingredient.

As an example, the following compositions can be formulated: Coated pill: active ingredient: 100 mg. Excipients:magnesium stearate, lactose, talcum, starch, alginic acid, hydroxypropylcellulose. Bottle: active ingredient: 1000 mg in freeze-dried form desolved in 20 ml of water for administration by injection.

The preferred doses are 1 mg/kg to 300 mg/kg by bolus injection and 0.02 mg/kg/min to 60 mg/kg/min by infusion. Of course, the dose will vary depending upon the age, weight, route of administration and physical condition of the recipient.

Pharmacological tests have been carried out on several types of tumor cells in a disk diffusion assay see, generally T. H. Corbett, et al., In Vitro and In Vivo Models of Detection of New Antitumor Drugs, L. J. Hanku, T. Konda and B. J. White, ed., Univ of Tokyo Press, pages 5-14 (1986). The fluorinated FAA (4-oxo-2-(3-fluorophenyl)-4H-1-benzopyran-8-acetic acid) of Example 1 was tested against human H125 lung cells and CX-1 colon cells, mouse cell lines C09, P02 and C38, leukemia L1210 cells and FAA resistant cell lines at various doses. The results are shown in the Table 1, below. A larger number indicates a greater zone of inhibition and thus more antitumor effectiveness.

TABLE 1

| Test | Dose μg/disk | Leukemia L1210 | Mouse | | | Human | | FAA Resistant |
|------|------|------|------|------|------|------|------|------|
| | | | CO9 | PO3 | C38 | H125 | CX-1 | |
| 1 | 2000 | 460 | 600 | — | — | — | 320 | — |
| 2 | 1000 | 260 | — | 280 | 150 | 200 | 0 | 240 |
| 3 | 500 | 140 | — | 220 | 240 | 0 | — | 200 |
| 4 FAA | 1000 | 400–520 | — | 600–950 | — | 0 | 0 | 0 |
| 5 FAA | 500 | 0–40 | — | 240 | 400 | 0 | 0 | 0 |

Table 1 shows the fluorinated FAA compound (Tests 1-3) to have a dose related anti-tumor activity against leukemia L1210 cells and the various mouse and human cell lines. Especially interesting is the activity demonstrated against the normally FAA resistant cell line at the 1000 and 500 μg/disk dosages and, in particular, against human colon cell line CX-1 at 2000 μg/disk and the human lung line H125 at 1000 μg/disk dosages. Also, it is demonstrated that the FAA (4-oxo-2-phenyl-4H-1-benzopyran-8-acetic acid) controls (Tests 4-5) showed no activity against the human cell lines and the FAA resistant cell line. It is also recognized that while the FAA controls show activity against the mouse cell lines they have been known to not show activity against human cell lines as demonstrated here.

In a separate experiment the fluorinated FAA compound of Example 1 was tested for cytotoxicity against murine and human tumor cells in the disk diffusion assay. These results are shown in Table 2. Each disk was treated with 1000 μg per disk of the fluorinated FAA compound.

TABLE 2

| Test | Mouse | | | FAA Resistant Cell Line | Human | | | |
|---|---|---|---|---|---|---|---|---|
| | L1210 | Colon 08 | Colon 07 | | Colon 116 | Colon CX-1 | HCT8 | Lung H125 |
| 1 | 440 | 600 | 600 | 350 | 370 | 370 | — | 370 |
| 2 | 270–320 | 600 | 240 | 230 | 320 | — | 280 | — |

The results in Table 2 indicate that the subject compound of Example 1 had good activity in vitro against three human tumor colon cell lines (116, CX-1 and HCT8) and a human tumor lung line, H125.

The fluorinated FAA compound of Example 1 was also tested in vivo in mice. Escalating dosages were administered to mice having colon adenocarcinoma 38. The maximum dosage tolerated per IV injection was between 150 to 220 mg/kg. The first dosage of about 100 mg/kg produced a stupor but subsequent dosages escalated to 150 mg/kg were well tolerated. The fluorinated FAA (tests 1 and 2) was obviously active against Colon 38 as shown in Table 3, below, versus a Control which was tumored mice receiving no drug treatment.

pound which showed modest stupor in mice after higher dose injections of about 180 mg/kg.

For example, the fluorinated FAA of Example 1 produced shallow rapid breathing and modest stupor. The dosages were escalated to produce evident toxicity. At about 180 mg/kg one out of five mice tested were killed. The compound showed activity against tumors as three out of five mice were tumor free on the 35th day. The remaining mouse had a very small mass of 32 mg which may not have been viable tumor cells. Meanwhile, in the control group where no treatment was given all six mice exhibited a median tumor of 1852 grams on the 28th day and were not tumor free on the 35th day.

TABLE 3

| Test | # Mice | Dosage mg/kg | Days Injected | Drug Deaths | Median Tumor mg/on day 31 | T/C in % | Tumor Free at day 60 |
|---|---|---|---|---|---|---|---|
| 1 | 5 | 220 | 3 | 3 | 44 | 3 | 1 |
| 2 | 5 | 150 | 6, 9, 12, 15 | 0 | 448 | 32 | 2 |
| Control | 6 | 0 | — | 0 | 1383 | — | 0 |

Additionally, BDF$_1$ mice were treated for early stage pancreatic ductal adenocarcinoma 03. These tests are shown in Tables 4 and 5 below.

TABLE 4

| Test | Drug | Dose mg/kg/injection | Total Dosage | Drug Deaths | Tumor Free on Day 26 |
|---|---|---|---|---|---|
| 1 | FAA | 235 | 205 | 5/5 | Toxic |
| 2 | FAA | 162 | 486 | 1/5 | 4/5 |
| 3 | FAA | 112 | 336 | 0/5 | 1/5 |
| 4 | Ex. 1* | 155 | 465 | 4/6 | 2/6 |
| 5 | Ex. 1* | 107 | 321 | 0/6 | 3/6 |
| 6 | Ex. 1* | 74 | 222 | 0/5 | 0/5 |
| 7 | Control | 0 | 0 | 0/6 | 0/6 |

*Compound of Example 1, 4-oxo-2-(3-fluorophenyl)-4H-1-benzopyran-8-acetic acid.

The data in Table 4 indicates that at the lower dosage level of 321 mg/kg the fluorinated FAA was more potent as an antitumor drug than FAA.

TABLE 5

| Test | Drug | Dose mg/kg/injection | Total Dosage | Drug Deaths | Tumor Free on Day 26 |
|---|---|---|---|---|---|
| 1 | Ex. 4* | 80 on day 3<br>100 on day 5<br>150 on day 7 | 330 | 0/5 | 3/5 |
| 2 | Ex. 5** | 90 on day 3<br>110 on day 5<br>160 on day 7 | 360 | 0/5 | 4/5 |

*Compound of Example 4, 4-oxo-2-(2-fluorophenyl)-4H-1-benzopyran-8-acetic acid.
**Compound of Example 5, 4-oxo-2-(4-fluorophenyl)-4H-1-benzopyran-8-acetic acid.

Both drugs used in tests 1 and 2 were effective in the treatment of tumors. Interesting was that these drugs did not cause a stupor even at the higher dosage injections. The mice were repeatedly checked up to 3 hours post injection and no stupor was observed. This is in sharp contrast to FAA and even the Example 1 com-

EXAMPLE 1

Preparation of 4-oxo-2-(3-fluorophenyl)-4H-1-benzopyran-8-acetic acid.

Step 1

A mixture of 60 g of o-cresol and 153 g of ethyl 3-fluorobenzoylacetate was added over 30 minutes to a mechanically stirred solution of 750 g of polyphosphoric acid. The resulting mixture was stirred at 75° C. for 4 hours, then cooled and poured into 8 liters of ice water and subsequently extracted with three four liter portions of ethyl acetate. The solvent in the organic fractions was concentrated in vacuo and the residue chromatographed over 7 kg of silica gel eluting with 20% acetone in hexane to give 23 g of title product which was then recrystallized from ethyl acetate to give 16 g of pure 8-methyl-2-(3-fluorophenyl)-4H-benzopyran-4-one. TLC Rf 0.3 in 10% acetone in hexane; NMR (CDCl$_3$) δ 2.6 (s, 3H), 6.8 (s, 1H), 8.04–8.08 (m, 1H).

Steps 2 and 3

A mixture of 14.3 g of 8-methyl-2-(3-fluorophenyl)-4H-benzopyran-4-one, 17.2 g of N-bromosuccinimide and 3.5 g of azobisisobutyronitrile (AIBN) in 700 ml of carbon tetrachloride was refluxed for 6.5 hours, cooled to room temperature and stirred overnight and then diluted with 100 ml of water. The solvents were removed in vacuo and the residue recrystallized from hot ethyl acetate to give 16.5 g of 8-bromomethyl-2-(3-fluorophenyl)-4H-benzopyran-4-one which was used without further purification.

A suspension of 11.2 g of the above prepared 8-bromomethyl-2-(3-fluorophenyl)-4H-benzopyran-4-one, 3.2 g of potassium cyanide, 5.7 g of potassium iodide and 1.3 g of aliquot 336 (tricaprylylmethylammonium chloride) in 45 ml of water and 485 ml of toluene was stirred for 25.5 hours at 73° C., cooled, diluted with water and extracted with methylene chloride. The solvents in the organic layer were concentrated in vacuo and the resulting residue chromatographed over silica gel with 3-5% acetone in a 1:1 mixture of methylene chloride and hexane to give 4.6 g of 8-cyanomethyl-2-(3-fluorophenyl)-4H-benzopyran-4-one. IR 1643 cm$^{-1}$; NMR (CDCl$^3$): δ 4.06 (2, 1H), 6.8 (s, 1H), 7.0-7.85 (m, 6H), 8.2 (m, 1H).

Step 4

A mixture of 4.6 g of 8-cyanomethyl-2-(3-fluorophenyl)-4H-benzopyran-4-one; 18 ml of glacial acetic acid and 18 ml of sulfuric acid in 418 ml of water was stirred 12 hours at room temperature and diluted with 200 ml of water. The resulting suspension was filtered and the solids washed with water, then dissolved in 170 ml of 5% aqueous sodium bicarbonate, filtered to removed insoluble solids and acidified by addition of 11 ml of concentrated sulfuric acid. The resulting precipitate was filtered and the solids washed with water and dried to give 4.4 g of 4-oxo-2-(3-fluorophenyl)-4H-1-benzopyran-8-acetic acid as a white solid: IR 1645 and 1700 cm$^{-1}$; m.p. 208°-211° C.

EXAMPLE 2

Preparation of
4-oxo-2-(3,4-difluorophenyl)-4H-1-benzopyran-8-acetic acid.

Step 1

A suspension of 6.2 g of potassium hydroxide, 10 g of 2-hydroxyacetophenone and 17.8 g of allyl bromide in 550 ml of acetone was refluxed for 16 hours, cooled and filtered. The solids were extracted with three 250 ml portions of chloroform and the combined acetone filtrate and chloroform extracts concentrated to give a residue which was then heated at 165° C. for 18 hours, cooled, diluted with 250 ml of hexane and filtered. The resulting filtrate was concentrated in vacuo to give 10.02 g of 3'-allyl-2'-hydroxyacetophenone as a liquid: TLC Rf 0.70 in 3:1 toluene-methyl isobutylketone; C-13 NMR (CDCl$_3$): δ26.72, 33.41, 116.0, 118.44, 119.21, 128.82, 129.34, 136.10, 136.44, 160.40, 204.75; $^1$H-NMR (CDCl$_3$): δ2.60 (s, 3H), 3.40 (d, J=6.4 Hz, 2H); 5.05 (d, J=1.4 Hz, 1H), 5.08-5.11 (m, 1H), 5.92-6.06 (m, 1H), 6.82 (t, J=7.6 Hz, 1H), 7.33 (d, J=6.7 Hz, 1H), 7.59 (d, J=6.7 Hz, 1H), 12.62 (s, 1H).

Step 2

A mixture of 1.7 g (9.4 mmol) of 3'-allyl-2'-hydroxyacetophenone, 2.0 g (11 mmol) of 3,4-difluorobenzoyl chloride, 1.6 g (4.7 mmol) of tetra-n-butylammonium bisulfate, 60 ml of 10% aqueous potassium hydroxide and 60 ml of benzene was heated at 60° C. for 4 hours, cooled and the phases separated. The organic phase was washed with three 60 ml portions of water, treated with 5.6 g (28 mmol) of p-toluenesulfonic acid monohydrate and an additional 60 ml of benzene and refluxed for 3 hours, using a Dean-Stark trap to remove the water in the reaction. The resulting mixture was washed with 150 ml of 8% aqueous sodium bicarbonate and then with three 60 ml portions of water. The organic phase was then concentrated in vacuo; treated with 25 ml of methanol and cooled to −20° C. After four hours the resulting solid was filtered, washed with three 5 ml portions of methanol and dried to give 1.62 g (56%) of 8-allyl-2-(3,4-difluorophenyl)-4H-benzopyran-4-one as a solid: m.p. 127°-130° C.; TLC Rf 0.48 in 3:1 toluene-methyl isobutyl ketone.

Step 3

A mixture of 1.0 g (3.4 mmol) of 8-allyl-2-(3,4-difluorophenyl)-4H-benzopyran-4-one, 3.6 g (17 mmol) of sodium periodate, 7 ml of carbontetrachloride, 7 ml of acetonitrile and 15 ml of water was treated with 0.14 g (0.66 mmol) of rothenium (III)·chloride, stirred for 4 hours and then diluted with 50 ml of methylene chloride. The phases were separated and the aqueous phase extracted with three 50 ml portions of methylene chloride. The combined organic phases were concentrated in vacuo, treated with 500 ml of diethyl ether and filtered. The resulting solids were extracted with three 100 ml portions of 8% aqueous sodium bicarbonate solution and the aqueous extract washed with three 100 ml portion of chloroform. The aqueous phase was treated with concentrated hydrochloric acid (to pH 1) and then extracted with three 100 ml portions of chloroform. The final chloroform extract was evaporated in vacuo to give 0.131 g (12%) of 4-oxo-2-(3,4-difluorophenyl)4H-1-benzopyran-8-acetic acid as a solid: m.p. 145°-147° C.; TLC Rf 0.26 in 64:25:10:1 toluene-methylisobutylketone-methanol-acetic acid.

EXAMPLE 3

Preparation of
4-oxo-2-(pentafluorophenyl)-4H-1-benzopyran-8-acetic acid

Step 1

A mixture of 19 g (mmol) 3'-allyl-2'-hydroxyacetophenone, 25 g (110 mmol) pentafluorobenzoyl chloride, 36 g (110 mmol) tetra-n-butylammonium bisulfate, 750 ml 10% aqueous KOH, and 750 ml benzene was heated at 80° C. for 6 hours, cooled and the phases separated. The organic phase was concentrated in vacuo and flash chromatographed over 100 g silica gel with success, 2 liter portions of hexane, diethyl ether and CHCl$_3$. The diethyl ether eluate was evaporated in vacuo. The residue was dissolved in 250 ml methanol and cooled at −20° C. for 24 hours. The mixture was filtered and yielded 8-allyl-2-(pentafluorophenyl)-4H-benzopyran-4-one as 10.141 g (27%) solid: TLC R$_f$0.35 in 49:25:25:1 CHCl$_3$:toluene:hexane:methanol.

Step 2

A mixture of 2.0 g (5.7 mmol) 8-allyl-2-pentafluorophenyl)-4H-benzopyran-4-one, 5.8 g (27 mmol) NaIO$_4$, 0.091 g (0.36 mmol) RuCl$_3$·H$_2$O, 50 ml CH$_3$CN, 50 ml CCl$_4$ and 100 ml H$_2$O was stirred at room temperature. After 5 hours, 300 ml CHCl$_3$ was added to the mixture and the phases were separated. The aqueous phase was extracted with 500 ml 9:1 CHCl$_3$:CH$_3$OH and 400 ml H$_2$O was added to the aqueous phase. This aqueous phase was extracted with two 500 ml portions 9:1 CHCl$_3$:CH$_3$OH. The combined organic extracts were concentrated in vacuo to approximately 25 m and added to 1 liter of hexane. The mixture was filtered in vacuo and the filtered solids were redissolved and precipitated in hexane two more times. This yielded 0.259 g (12%) of 4-oxo-2-(pentafluorophenyl)-4H-1-benzopyran-8-acetic acid as a solid: m.p. 156°-160° C.; TLC R$_f$ 0.23 in 24:25:10:1 toluene:methylisobutylketone:methanol:acetic acid.

EXAMPLE 4

Preparation of
4-oxo-2-(2-fluorophenyl)-4H-1-benzopyran-8-acetic acid

Step 1

A mixture of 0.528 g (3 mmol) of 3'-allyl-2'-hydroxyacetophenone, 0.57 g (3.6 mmol) of 2-fluorobenzoyl chloride, 0.509 g (1.5 mmol) of tetra-n-butylammonium bisulfate, 20 ml of 10% aqueous potassium hydroxide and 20 ml of benzene was heated at 80° C. for 3 hours. The layers were separated and the benzene layer washed thoroughly with water (3×20 ml) and the water removed from the benzene layer by azeotropic distillation. The resulting residue was treated with 1.7 g (9 mmol) of p-toluenesulphonic acid and benzene (25 ml) and heated for two hours with azeotropic removal of water. The benzene solution was washed with 8% aqueous sodium bicarbonate (50 ml) and the solvent evaporated in vacuo. The resulting residue was recrystallized from ethyl acetate to give 0.49 g (58%) of 8-allyl-2-(2-fluorophenyl)-4H-benzopyran-4-one as white solid: M.P. 78°-81° C.; TLC $R_f$ 0.40 in 10:1 hexane-ethylacetate.

Step 2

A mixture of 1.4 g (5 mmol) of 8-allyl-2-(2-fluorophenyl)-4H-benzopyran-4-one, 4.4 g (20.5 mmol) of sodium periodate, 50 ml of carbon tetrachloride, 50 ml of acetonitrile, and 75 ml of water was treated with 0.025 g (2.2% mol) of ruthenium trichloride hydrate. The entire mixture was stirred vigorously for 2 hours at room temperature and the phases were separated. The upper aqueous phase was extracted with three 50 ml portions of methylene chloride. The combined organic extracts were washed with 30 ml of 10% aqueous sodium bisulfite solution and then extracted with three 50 ml portions of 10% aqueous sodium hydroxide solution. The aqueous phase was treated with concentrated hydrochloride acid (to pH 1) and then extracted with three 100 ml portions of ethyl acetate. The extracts were dried over magnesium sulfate and concentrated in vacuo to give yellow solid which was recrystallized in methanol to give 0.274 g (18%) of 4-oxo-2-(2-fluorophenyl)-4H-1-benzopyran-8-acetic acid as a white solid: M.P. 179°-181° C.; TLC $R_f$ 0.29 in 40:40:1 hexane-ethylacetate-acetic acid.

EXAMPLE 5

Preparation of
4-oxo-2-(4-fluorophenyl)-4H-1-benzopyran-8-acetic acid

Step 1

The same procedure as used in Example 4 was used to prepare this compound. Starting from a 3 mmol scale, 0.375 g (45%) of 8-allyl-2-(4-fluorophenyl)-4H-benzopyran-4-one was obtained as a white solid: M.P. 98°-100° C.; TLC $R_f$ 0.38 in 10:1 hexane-ethyl acetate.

Step 2

A similar procedure as used in Example 4 was used employing 6 equivalents of sodium periodate and 3.3 mol % of ruthenium trichloride for 1.5 hours at room temperature to give 0.075 g (25%) of 4-oxo-2-(4-fluorophenyl)-4H-1-benzopyran-8-acetic acid as white crystals: M.P. 207°210° C.

EXAMPLE 6

Preparation of
4-oxo-2-(2',3',4',5'-tetrafluorophenyl)-4H-1-benzopyran-8-acetic acid.

Step 1

A mixture of 25 g (130 mmol) 2,3,4,5-tetrafluorobenzoic acid, 0.5 ml DMF, 200 ml $CH_2Cl_2$ and 17 ml (192 mmol) oxalyl chloride was stirred at room temperature for 21 hours. The mixture was filtered and evaporated in vacuo. The concentrate was extracted with 3×300 ml hexane. The extract was filtered via gravity through a coarse pore sintered glass funnel. This filtrate was evaporated in vacuo to yield 22 g (76%) of 2,3,4,5-tetrafluorobenzoylchloride as a colorless liquid. $^1$H-NMR($CDCl_3$) δ281-289 (m, 1H); $^{13}$C-NMR($CDCl_3$): δ114.882 (d, J=21.7 Hz), 141.300 (d, J=270.0 Hz), 144.763 (d, J=279 Hz), 146.303 (d, J=241 Hz), 147.595 (d, J=279 Hz), 160.593.

Step 2

A mixture of 19.3 g (110 mmol) 3'-allyl-2'-hydroxyacetophenoxy 22 g (110 mmol) 2,3,4,5-tetrafluorobenzoyl chloride, 38.4 g (110 mmol) tetra-n-butylammonium bisulfate, 750 ml 10% aqueous KOH and 750 ml benzene was heated at 80° C. for 6 hours, cooled and the phases were separated. The organic phase was concentrated in vacuo and flash chromatographed over 100 g silica gel with successive 2 l portions of hexane and 9:1 $CHCl_3$:$CH_3OH$. The $CHCl_3$:$CH_3OH$ eluate was concentrated in vacuo, treated with 500 ml hot $CH_3OH$ and cooled to −20° C. After 24 hours, the resulting solid was filtered, washed with three 25 ml portions of cold methanol and dried to give 5.35 g of 8-allyl-2-(2,3,4,5-tetrafluorophenyl)-4H-benzopyran-4-one as a solid: TLC $R_f$ 0.37 in 49:25:25:1 $CHCl_3$:toluene:hexane:$CH_3OH$; $^1$H-NMR (DMSO) δ3.44 (d, J=6.5 Hz, 2H), 5.06 (s, 1H), 5.09-5.10 (m, 1H), 5.92-6.09 (m, 1H), 6.94 (s, 1H), 7.00 (t, J=9.6 Hz, 1H), 7.31 (d, J=7.4 Hz, 1H), 7.55 (d, J=7.8 Hz, 1H), 7.82-7.88 (m, 1H); $^{13}$(-NMR (DMSO) δ35.376, 107.823 (d, J=18.9 Hz), 112.735, 117.685, 120.791, 121.10, 121.686, 129.056, 130.408, 135.025, 138.032, 141.300 (d, J=270 Hz), 144.763 (d, J=279 Hz), 146.303 (d=241 Hz), 147.595 (d, J=279 Hz), 154.957, 164.706, 176.488.

Step 3

A mixture of 2.0 g (6.0 mmol) of 8-allyl-2-(2,3,4,5-tetrafluorophenyl)-4H-benzopyran-4-one, 6.4 g (30 mmol) $NaIO_4$, 0.100 (0.40 mmol) $RuCl_3.H_2O$, 50 ml $CCl_4$, 50 ml $CH_3CH$ and 100 ml $H_2O$ was stirred at room temperature. After 5 hours, 300 ml $CHCl_3$ was added and the phases separated. The aqueous phase was extracted with 500 ml 9:1 $CHCl_3$:$CH_3OH$. An additional 400 ml $H_2O$ was added to the aqueous phase which was then extracted with two 500 ml portions of 9:1 $CNCl_3$:$CH_3OH$. The combined organic extracts were concentrated in vacuo to approximately 25 ml and added to 1 l of hexane. The mixture was filtered in vacuo and the filtered solids were redissolved and precipitated in hexane two more times. This yielded 0.345 g of 4-oxo-2-(2,3,4,5-tetrafluorophenyl-4H-1-benzopyran-8-acetic acid as a solid: M.P. 154°-159° C.

EXAMPLE 7

Preparation of 4-oxo-2-(2,6-difluorophenyl)-1H-1-benzopyran-8-acetic acid

Step 1

The same procedure as used in Example 4 was used to give 8-allyl-2-(2,6-difluorophenyl)-4H-benzopyran-4-one as pale yellow crystals in 35% yield: M.P. 84°–86° C.; TLC $R_f$ 0.45 in 10:1 hexane-ethyl acetate.

Step 2

A similar procedure as used to prepare 4-oxo-2-(2-fluorophenyl)-4H-1-benzopyran-8-acetic acid in Example 4 was used, employing 6 equivalents of sodium periodate and 3.3 mol % of ruthenium trichloride for 1.5 hours at 0° C. to give 4-oxo-2-(2,6-difluorophenyl)-4H-1-benzopyran-8-acetic acid in 35% yield as white crystals: M.P. 178°–180° C.; TLC $R_f$ 0.27 in 40:40:1 hexane-ethyl acetate-acetic acid.

EXAMPLE 8

Preparation of 4-oxo-2-(3,5-difluorophenyl)-4H-1-benzopyran-8-acetic acid

Step 1

The same procedure as used in Example 4 was used to prepare 8-allyl-2-(3,5-difluorophenyl)-4H-1-benzopyran-4-one in 38% yield as white crystals: M.P. 152°–155° C.; TLC $R_f$ 0.35 in 10:1 hexane-ethyl acetate.

Step 2

A similar procedure as used to prepare 4-oxo-2-(2-fluorophenyl)-4H-1-benzopyran-8-acetic acid in Example 4 was used, employing 5 equivalents of sodium periodate and 3.3 mol % of ruthenium trichloride for 1.5 hours at room temperature to give 4-oxo-2-(3,5-difluorophenyl)-4H-1-benzopyran-8-acetic acid as white crystals in 16% yield: M.P. 221°–223° C.; TLC $R_f$ 0.29 in 40:40:1 hexane-ethyl acetate-acetic acid.

EXAMPLE 9

Preparation of 4-oxo-2-(2,5-difluorophenyl)-4H-1-benzopyran-8-acetic acid

To a 500 ml flask was added 20 g (165.3 mmol) allylbromide, 20 g (147 mmol) 2-hydroxyacetophenone, 10 g (178.6 mmol) potassium hydroxide and 250 ml acetone. The mixture was stirred and refluxed for 6 hours. The resulting suspension was filtered, and the filtered solid was washed with ethyl acetate (3×100 ml). The filtrate was evaporated in vacuum to give 27.8 g of an allyl ether as a yellow oil. The crude allyl ether was directly heated neat at 220° C. (oven temperature) for 72 hours under $N_2$. The reaction product was collected as a pale yellow oil after vacuum distillation (b.p. 105°–115° C. at 1 mm) to give 24.4 g (94%) of 3-allyl-2-hydroxyacetophenone.

To a 100 ml flask fitted with a calcium chloride drying tube was added 5.5 g (31.2 mmol) of 3-allyl-2-hydroxyacetophenone, 5 g (28.4 mmol) of 2,5-difluorobenzoyl chloride, 5 ml of $Et_3N$ and 10 ml of pyridine. The temperature of the reaction mixture rose spontaneously. The stirred reaction mixture was heated at 70° C. for one hour. The mixture was cooled and poured into 200 ml of 5% HCl with stirring and extracted with EtOAc (3×50 ml). The combined organic layers were washed with $H_2O$ and dried over $MgSO_4$, and then concentrated to give 9.5 g of 2,5-difluoro-flavone acetic acid as a yellow crude oil. The crude product was directly used in next step without further purification.

To a one liter round-bottom flask containing 200 ml of $CH_3CN$, 200 ml of $CCl_4$ and 300 ml of water was added 9.4 g (28.4 mmol) of crude 2,5-difluoro-flavone acetic acid, 31.1 g (5.12 eq) of $NaIO_4$ and 290 mg (0.044 eq) of $RuCl_3.H_2O$. After stirring vigorously for 2.5 hours at room temperature, the organic layer was separated, and the aqueous layer was extracted with $CH_2Cl_2$ (100 ml×3). The combined organic layers were washed with 10% aq $Na_2SO_3$ solution (50 ml) and brine, dried over $MgSO_4$, and concentrated to give 10.5 g of crude acid product.

To a warmed 15 ml pyridine solution of 10.5 g (28.4 mmol) of the crude acid product was added 4.97 g (80%, 2.5 eq) of pulverized KOH. The resulting mixture was heated to 70° C. and stirred for 1 hour during which time much precipitate formed. The mixture was cooled and acidified with 250 ml of 5% aqueous HCl solution. The crude diketone formed was separated as yellow precipitate which was collected on a filter and dried to give 5.2 g (54%) of crude product.

To a solution of 5.2 g of the crude diketone in 50 ml of glacial acetic acid was added 2 ml of concentrated $H_2SO_4$ with stirring. The resulting mixture was heated to 100° C. for 1 hour and then poured onto 300 g ice with vigorous stirring. The crude final product was collected on a filter, washed with $H_2O$ (300 ml) and recrystallized in MeOH to give 1.58 g of 4-oxo-2-(2,5-difluorophenyl)-4H-1-benzopyran-8-acetic acid as white crystals with an overall yield of 17% from 2,5-difluorobenzoyl-chloride. M.P. 223°±1° C.

FORMULAS

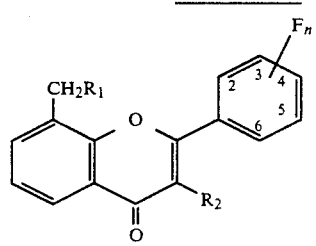

FORMULA I

SCHEME 1
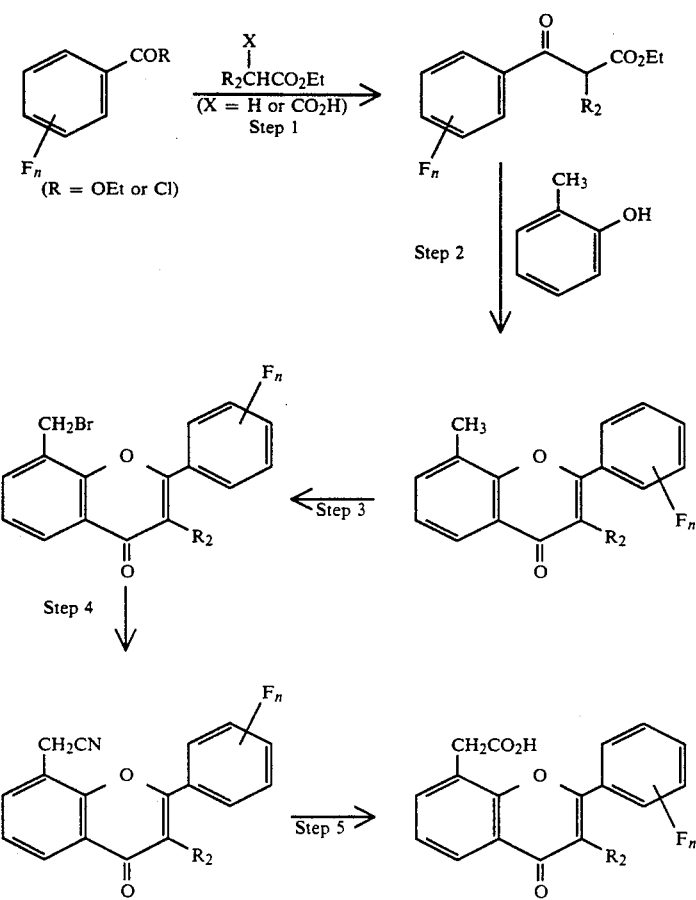
SCHEME 2
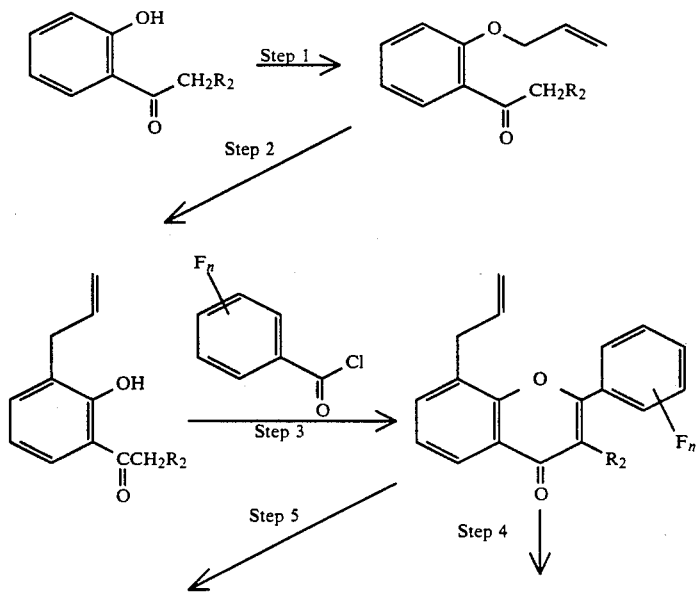

SCHEME 2

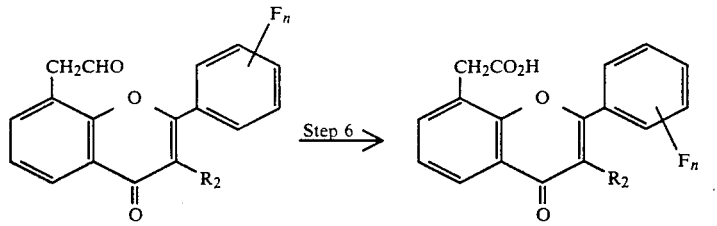

I claim:
1. A compound comprising:

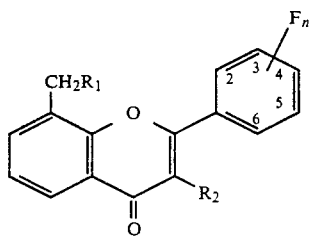

FORMULA I wherein
$R_1$ is CHO, CN, $CO_2M$, $CO_2R_3$ or $CONR_3R_4$ where M is a pharmaceutically acceptable salt;
$R_2$ is hydrogen, fluorine, methyl, $CF_3$, phenyl or phenyl substituted with a F, Cl, Br, OH or $C_{1-4}$ alkyl group;
$R_3$ and $R_4$ are independently hydrogen, $C_1$-$C_{12}$ alkyl, $C_3$-$C_{10}$ cycloalkyl, $C_6$-$C_{12}$ aryl, $C_7$-$C_{24}$ alkylaryl, a piperidine whose nitrogen atom can be substituted with a $C_{1-4}$ alkyl, $C_{6-12}$ aryl or $C_{3-10}$ cycloalkyl, or a morpholine whose nitrogen atom can be substituted with a $C_{1-4}$ alkyl, $C_{6-12}$ aryl or $C_{3-10}$ cycloalkyl, or $R_3$ and $R_4$ together with the nitrogen atom to which they are attached form a piperidine or morpholine; and
n is 1 to 5, inclusive.

2. The compound of claim 1 wherein $R_1$ is $CO_2M$.
3. The compound of claim 2 wherein $R_2$ is hydrogen.
4. The compound of claim 1 wherein said fluorine is positioned on said phenyl to form:
a) 2-fluorophenyl;
b) 2,6-difluorophenyl;
c) 2,3,4,5-tetrafluorophenyl;
d) 3-fluorophenyl;
e) 3,4-difluorophenyl;
f) 3,5-difluorophenyl;
g) 4-fluorophenyl;
h) pentafluorophenyl;
i) 3,4,5-trifluorophenyl;
j) 2,3,5,6-tetrafluorophenyl;
k) 2,3-difluorophenyl;
l) 2,3,4-trifluorophenyl;
m) 2,4,6-trifluorophenyl;
n) 2,5-difluorophenyl; or
o) 2,4-difluorophenyl.

5. The compound of claim 1 which is:
a) 4-oxo-2-(2-fluorophenyl)-4H-1-benzopyran-8-acetic acid;
b) 4-oxo-2-(2,6-difluorophenyl)-4H-1-benzopyran-8-acetic acid;
c) 4-oxo-2-(2,3,4,5-tetrafluorophenyl)-4H-1-benzopyran-8-acetic acid;
d) 4-oxo-2-(3-fluorophenyl)-4H-1-benzopyran-8-acetic acid;
e) 4-oxo-2-(4-fluorophenyl)-4H-1-benzopyran-8-acetic acid;
f) 4-oxo-2-(3,5-difluorophenyl)-4H-1-benzopyran-8-acetic acid;
g) 4-oxo-2-(3,4-difluorophenyl)-4H-1-benzopyran-8-acetic acid;
h) 4-oxo-2-(pentafluorophenyl)-4H-1-benzopyran-8-acetic acid;
i) 4-oxo-2-(3,4,5-trifluorophenyl)-4H-1-benzopyran-8-acetic acid;
j) 4-oxo-2-(2,3,5,6-tetrafluorophenyl)-4H-1-benzopyran-8-acetic acid;
k) 4-oxo-2-(2,3-difluorophenyl)-4H-1-benzopyran-8-acetic acid;
l) 4-oxo-2-(2,3,4-trifluorophenyl)-4H-1-benzopyran-8-acetic acid;
m) 4-oxo-2-(2,4,6-trifluorophenyl)-4H-1-benzopyran-8-acetic acid;
n) 4-oxo-2-(2,5-difluorophenyl)-4H-1-benzopyran-8-acetic acid; or
o) 4-oxo-2-(2,4-difluorophenyl)-4H-1-benzopyran-8-acetic acid.

6. A pharmaceutical composition comprising an effective amount of a compound according to

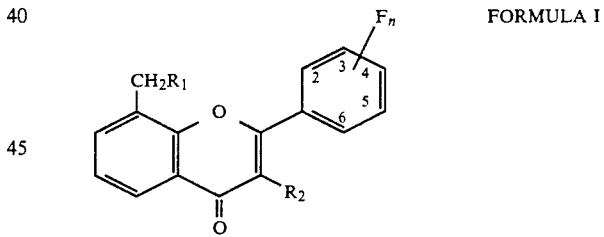

FORMULA I wherein
$R_1$ is CHO, CN, $CO_2M$, $CO_2R_3$ or $CONR_3R_4$ where M is a pharmaceutically acceptable salt;
$R_2$ is hydrogen, fluorine, methyl, $CF_3$, phenyl or phenyl substituted with a F, Cl, Br, OH or $C_{1-4}$ alkyl group;
$R_3$ and $R_4$ are independently hydrogen, $C_1$-$C_{12}$ alkyl, $C_3$-$C_{10}$ cycloalkyl, $C_6$-$C_{12}$ aryl, $C_7$-$C_{24}$ alkylaryl, a piperidine whose nitrogen atom can be substituted with a $C_{1-4}$ alkyl, $C_{6-12}$ aryl or $C_{3-10}$ cycloalkyl, or a morpholine whose nitrogen atom can be substituted with a $C_{1-4}$ alkyl, $C_{6-12}$ aryl or $C_{3-10}$ cycloalkyl, or $R_3$ and $R_4$ together with the nitrogen atom to which they are attached form a piperidine or morpholine; and
n is 1 to 5, inclusive.

7. The composition of claim 6 wherein $R_1$ is $CO_2M$.
8. The composition of claim 7 wherein $R_2$ is hydrogen.

9. The composition of claim 6 wherein said fluorine is positioned on said phenyl to form:
a) 2-fluorophenyl;
b) 2,6-difluorophenyl;
c) 2,3,4,5-tetrafluorophenyl;
d) 3-fluorophenyl;
e) 3,4-difluorophenyl;
f) 3,5-difluorophenyl;
g) 4-fluorophenyl;
h) pentafluorophenyl;
i) 3,4,5-trifluorophenyl;
j) 2,3,5,6-tetrafluorophenyl;
k) 2,3-difluorophenyl;
l) 2,3,4-trifluorophenyl;
m) 2,4,6-trifluorophenyl;
n) 2,5-difluorophenyl; or
o) 2,4-difluorophenyl.

10. The composition of claim 6 which is:
a) 4-oxo-2-(2-fluorophenyl)-4H-1-benzopyran-8-acetic acid;
b) 4-oxo-2-(2,6-difluorophenyl)-4H-1-benzopyran-8-acetic acid;
c) 4-oxo-2-(2,3,4,5-tetrafluorophenyl)-4H-1-benzopyran-8-acetic acid;
d) 4-oxo-2-(3-fluorophenyl)-4H-1-benzopyran-8-acetic acid;
e) 4-oxo-2-(4-fluorophenyl)-4H-1-benzopyran-8-acetic acid;
f) 4-oxo-2-(3,5-difluorophenyl)-4H-1-benzopyran-8-acetic acid;
g) 4-oxo-2-(3,4-difluorophenyl)-4H-1-benzopyran-8-acetic acid;
h) 4-oxo-2-(pentafluorophenyl)-4H-1-benzopyran-8-acetic acid;
i) 4-oxo-2-(3,4,5-trifluorophenyl)-4H-1-benzopyran-8-acetic acid;
j) 4-oxo-2-(2,3,5,6-tetrafluorophenyl)-4H-1-benzopyran-8-acetic acid;
k) 4-oxo-2-(2,3-difluorophenyl)-4H-1-benzopyran-8-acetic acid;
l) 4-oxo-2-(2,3,4-trifluorophenyl)-4H-1-benzopyran-8-acetic acid;
m) 4-oxo-2-(2,4,6-trifluorophenyl)-4H-1-benzopyran-8-acetic acid;
n) 4-oxo-2-(2,5-difluorophenyl)-4H-1-benzopyran-8-acetic acid; or
o) 4-oxo-2-(2,4-difluorophenyl)-4H-1-benzopyran-8-acetic acid.

* * * * *

UNITED STATES PATENT AND TRADEMARK OFFICE
CERTIFICATE OF CORRECTION

PATENT NO. : 5,238,954
DATED : Aug. 24, 1993
INVENTOR(S) : Paul A. Aristoff

It is certified that error appears in the above-indentified patent and that said Letters Patent is hereby corrected as shown below:

On title page, insert item [63] Related U.S. Application Data to read:

Continuation-in-part of Ser. No. 07/299,106, Jan 19, 1989, abandoned.

Signed and Sealed this

Fourteenth Day of June, 1994

*Attest:*

BRUCE LEHMAN

*Attesting Officer*     *Commissioner of Patents and Trademarks*